(12) United States Patent
Petros et al.

(10) Patent No.: US 7,094,199 B2
(45) Date of Patent: Aug. 22, 2006

(54) IVS OBTURATOR INSTRUMENT AND PROCEDURE

(75) Inventors: Peter Petros, Claremont (AU); Stuart Morton, Villepreux (FR)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 10/522,450

(22) PCT Filed: Jul. 23, 2003

(86) PCT No.: PCT/EP03/08067

§ 371 (c)(1),
(2), (4) Date: Jan. 20, 2005

(87) PCT Pub. No.: WO2004/008977

PCT Pub. Date: Jan. 29, 2004

(65) Prior Publication Data

US 2005/0261718 A1    Nov. 24, 2005

Related U.S. Application Data

(60) Provisional application No. 60/397,905, filed on Jul. 23, 2002.

(51) Int. Cl.
*A61F 2/00*        (2006.01)

(52) U.S. Cl. .......................................... 600/29; 606/139

(58) Field of Classification Search ............ 600/29–30, 600/37; 606/72, 75, 232, 185, 222, 139, 606/144, 148, 119; 227/175.1; 128/DIG. 25
See application file for complete search history.

(56) References Cited

U.S. PATENT DOCUMENTS 2,897,820 A    8/1959    Tauber
3,182,662 A    5/1965    Shirodkar
3,372,695 A    3/1968    Beliveau et al.

(Continued)

FOREIGN PATENT DOCUMENTS

WO        WO 0239890        5/2002

(Continued)

OTHER PUBLICATIONS

PCT International Search Report for International Application No. PCT/EP03/08067, date Nov. 17, 2003, (6 pgs).

*Primary Examiner*—John P. Lacyk

(57) ABSTRACT

There is disclosed a surgical instrument for inserting material into the body. The surgical instrument generally includes an outer tubular member. The instrument has a longitudinal section and an arcuate section having at least two different radii of curvature. An inner member is movably positioned within the outer tubular member and includes structure for engaging a length of material to draw the material through the outer tubular member and into the body. Methods of using the surgical instrument to position a length of tape beneath the urethra to form a support are also disclosed.

22 Claims, 19 Drawing Sheets

U.S. PATENT DOCUMENTS

| | | |
|---|---|---|
| 3,763,860 A | 10/1973 | Clarke |
| 3,924,633 A | 12/1975 | Cook et al. |
| 4,172,458 A | 10/1979 | Pereyra |
| 4,235,238 A | 11/1980 | Ogiu et al. |
| 4,392,495 A | 7/1983 | Bayers |
| 4,493,323 A | 1/1985 | Albright et al. |
| 4,509,516 A | 4/1985 | Richmond |
| 4,857,041 A | 8/1989 | Annis et al. |
| 5,112,344 A | 5/1992 | Petros |
| 5,281,237 A | 1/1994 | Gimpelson |
| 5,368,595 A | 11/1994 | Lewis |
| 5,403,328 A | 4/1995 | Shallman |
| 5,439,467 A | 8/1995 | Benderev et al. |
| 5,458,609 A | 10/1995 | Gordon et al. |
| 5,474,543 A | 12/1995 | McKay |
| 5,507,754 A | 4/1996 | Green et al. |
| 5,540,704 A | 7/1996 | Gordon et al. |
| 5,578,044 A | 11/1996 | Gordon et al. |
| 5,643,288 A | 7/1997 | Thompson |
| 5,662,664 A | 9/1997 | Gordon et al. |
| 5,899,909 A | 5/1999 | Claren et al. |
| 6,053,935 A * | 4/2000 | Brenneman et al. ........ 606/232 |
| 6,096,041 A * | 8/2000 | Gellman et al. .............. 606/72 |
| 6,273,852 B1 | 8/2001 | Lehe et al. |
| 6,491,703 B1 | 12/2002 | Ulmsten |
| 2002/0077526 A1 | 6/2002 | Kammerer et al. |

FOREIGN PATENT DOCUMENTS

| | | |
|---|---|---|
| WO | WO 03053252 | 7/2003 |

* cited by examiner

IVS OBTURATOR INSTRUMENT AND PROCEDURE

The present application claims the benefit of and priority to International Application Ser. No. PCT/EP2003/008067 filed on Jul. 23, 2003, which, in turn, claims the benefit of and priority to U.S. Provisional Application Ser. No. 60/397,905, filed on Jul. 23, 2002 and entitled IVS OBTURATOR, the entire contents of which are incorporated herein by reference.

BACKGROUND

1. Technical Field

The technical field relates to insertion instrumentation for inserting material into the body and, more particularly, to an insertion tool and method for inserting a support structure or material into the body to provide a support to the urethra.

2. Background of Related Art

One problem occurring in women due to the onset of advanced age or trauma is urinary stress incontinence. Several therapies have been developed to correct or alleviate this condition, such as, for example drug therapies and surgical procedures. In some cases it is necessary to implant a temporary or permanent structure to support the midline of the urethra to control discharge.

Several surgical procedures have been developed to position a support against the urethra. Many of these procedures require the use and installation of bone anchors to affix the ends of the support to the pubic bone. These procedures are fairly invasive and require complex instruments to install the bone anchors in the pubic bone.

One exemplary device and method of inserting, in a minimally invasive manner, a sling support within the body to support the urethra is disclosed in certain embodiments of U.S. Pat. No. 5,112,344 to Petros. The Petros reference discloses the use of an instrument to insert a length of tape through incisions in the abdomen and the vagina so that the tape supports the urethra. No bone anchors or other auxiliary structures are used to anchor the tape. While inserting the tape into the body using the instrument, the instrument passes through the patient's body on either side of the bladder. Although this instrument is designed to safely pass from the incision in the vagina to the incision in the abdomen, surgeons typically perform a cystoscopy to check the integrity of the bladder.

It is desirable to have other methods of inserting, in a minimally invasive manner, support structure or material into the body without having to pass an instrument through the body on either side of the bladder.

SUMMARY

According to the present invention, there is provided a surgical instrument for passing a material into a body in a minimally invasive procedure comprising:

a first member having a longitudinal section defining a longitudinal axis and an arcuate section extending distally from the longitudinal section, wherein:

a proximal portion of the arcuate section curves away from the longitudinal axis in a first direction and defines a first radius of curvature; and a portion of the arcuate section distal of the proximal portion curves toward the longitudinal axis in a second direction and defines a second radius of curvature. The shape of the first member facilitates the passing of the material into the body, in a minimally invasive procedure.

The shape of the first member enables a material to be placed inside the body in a minimally invasive procedure so that the material extends through the obturator foramen.

In certain preferred embodiments, the first member comprises a hollow outer tubular member. A stylet is at least partially movable within the outer tubular member and engageable with a material to pass the material within the body. The hollow outer tubular member and stylet enable the surgeon to remove the stylet from the outer tubular member and reinsert the stylet in the opposite position with respect to the outer tubular member. This structure also facilitates the placement of the material so that the material extends from a first side of the pelvis to a second side of the pelvis.

A proximal portion of the arcuate section curves away from the longitudinal axis in a first direction and defines a first radius of curvature. A distal portion of the arcuate section curves toward the longitudinal axis in a second direction and defines a second radius of curvature. A portion of the distal section desirably extends across the longitudinal axis in the second direction.

In certain embodiments, the distal portion of the arcuate section has a third radius of curvature, different from the second radius of curvature. The distal portion may have a central section and a distalmost section. The central section has the second radius and the distalmost section has the third radius. In certain embodiments, the second radius is larger than the third radius. In other embodiments, the second radius is smaller than the third radius.

The stylet is desirably flexible. In certain preferred embodiments, the stylet includes a slot at a first end for receipt of an end of a material. The stylet desirably includes a conical tip at a second end. A diameter of the conical tip may be greater than an inner diameter of the outer tubular member.

The outer tubular member desirably has a handle at a proximal end thereof. In certain preferred embodiments, the handle has a laterally extending portion. The arcuate section defines a first plane and the wing defines a second plane substantially perpendicular to the first plane.

The surgical instrument preferably includes a material and, in certain preferred embodiments, wherein the material comprises a generally flat tape. At least one end of the tape may be cut at an angle for ease of threading the tape into the stylet, in embodiments in which the stylet comprises a slot for receipt of the at least one end. The tape desirably comprises a material including multifilament strands, which may comprise polypropylene strands. The material may comprise a generally flat tape and the stylet may have a proximal end adapted to receive an end of the tape. The material may comprise an absorbable material.

The stylet is desirably positioned in the tubular member so that the proximal end of the stylet is located adjacent a proximal end of the tubular member. In certain preferred embodiments, the stylet has a distal end that is blunt. The distal end may comprise a blunt conical tip. In other embodiments, the stylet has a distal end that is sharp.

In the present invention, the surgical instrument for passing a material into a body in a minimally invasive procedure may have the arcuate section dimensioned and curved whereby when in use and in position in the body, the arcuate section extends from the skin over the obturator foramen, through the obturator foramen, to the vaginal wall. The shape of the first member facilitates the passing of the material into the body, in a minimally invasive procedure. The shape of the first member enables a material to be placed inside the body in a minimally invasive procedure so that the material extends through the obturator foramen.

BRIEF DESCRIPTION OF THE DRAWINGS

Various embodiments are described herein with reference to the drawings wherein.

DETAILED DESCRIPTION OF PREFERRED EMBODIMENTS

Figure 1:
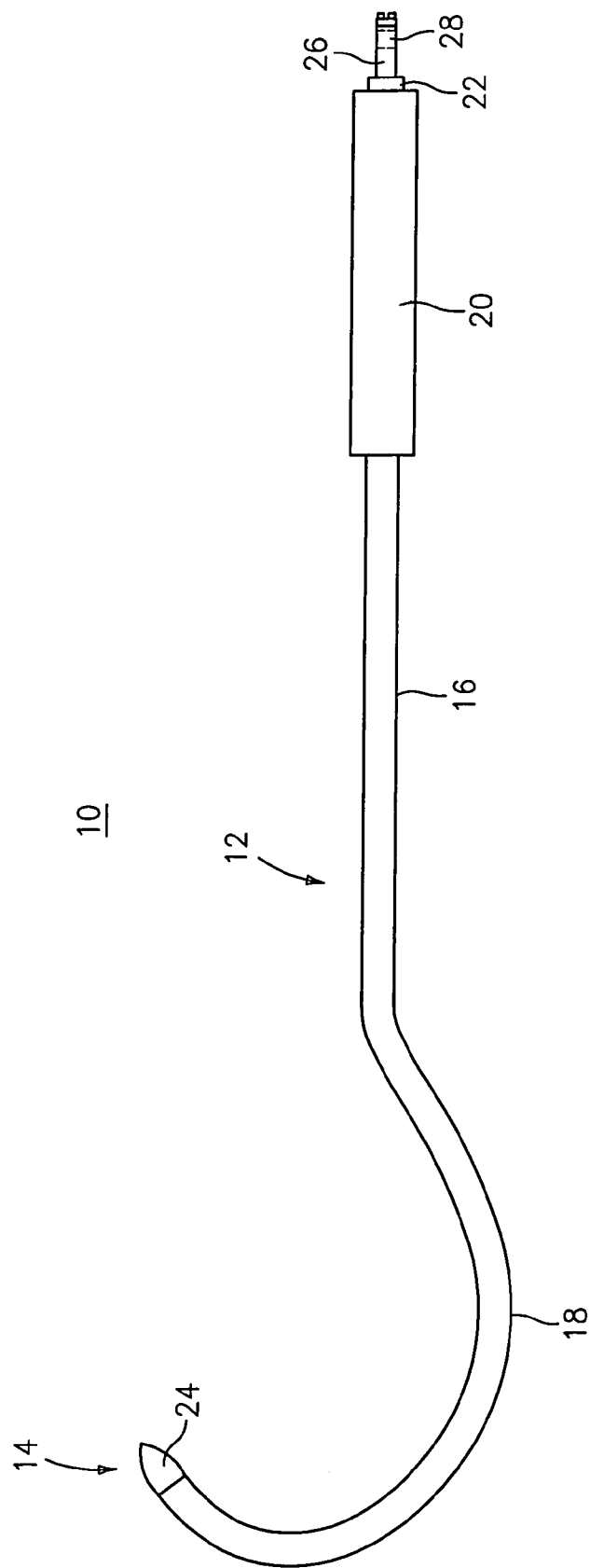
FIG. 1 is a side view of an instrument for use in a surgical procedure in accordance with an embodiment of the present invention.

A surgical instrument in accordance with an embodiment of the present invention is shown in FIGS. 1–50. The instrument 10 facilitates insertion of a length of material into the body, for example, in intravaginal slingplasty procedures. Instrument 10 generally includes an elongate hollow tubular outer member 12 and a generally flexible stylet 14 configured to pass at least partially within outer member 12. Outer member 12 includes a longitudinal section 16 and an arcuate section 18 extending distally from longitudinal section 16. Outer member 12 is preferably formed from a biocompatible material such as stainless steel. Outer member should have a smooth atraumatic surface to prevent trauma to tissue. A handle 20 is affixed to outer member 13 adjacent a proximal end 22 thereof.

Figure 2:
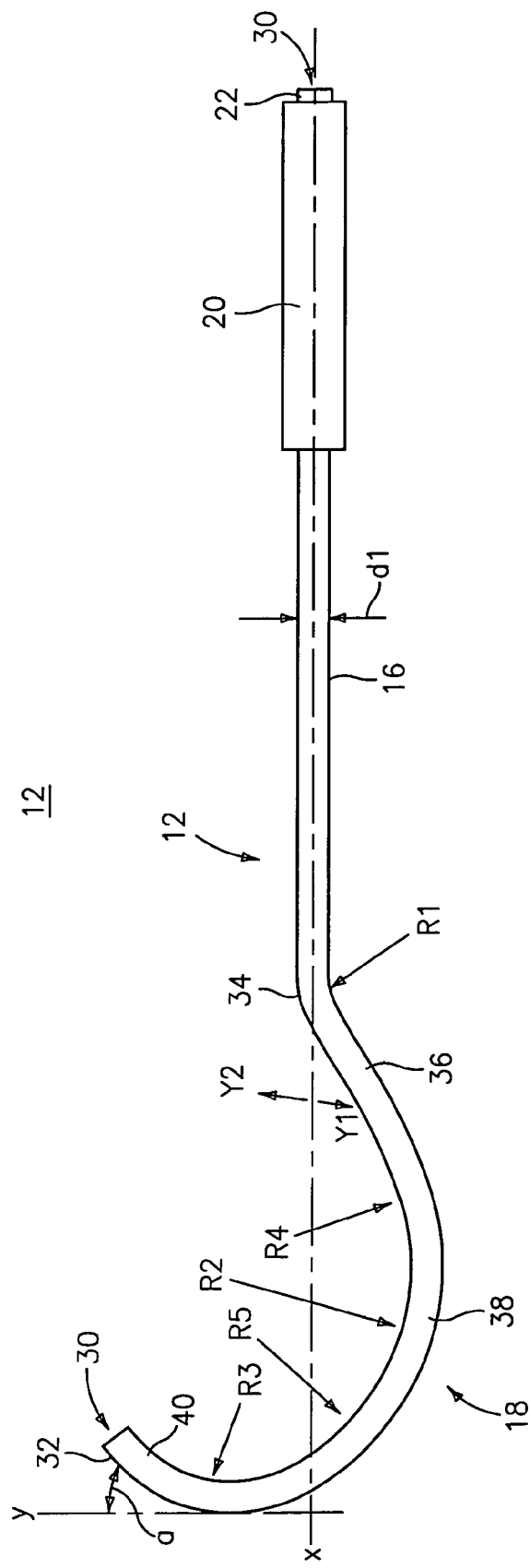
FIG. 2 is a side view of an outer member of the instrument in accordance with the embodiment of FIG. 1.

Referring now to FIG. 2, outer member 12 has a through bore 30 extending from proximal end 22 to a distal end 32 of outer member 12. Through bore 30 is preferably of a uniform diameter, having a uniform diameter d1. Longitudinal section 16 defines a longitudinal axis X. Outer member 12 has a shape that generally resembles a question mark. The arcuate section 18 includes a proximal portion 36, a central portion 38 and a distal portion 40. Proximal portion 36 extends away from longitudinal section 16 and away from the longitudinal axis X in a first direction Y1. The proximal portion 36 curves away from the longitudinal section 16 and has a radius R1. The central portion extends from the proximal portion 36 and extends toward the longitudinal axis X in a second direction Y2, opposite from the first direction. The central portion curves toward the longitudinal axis X and has a radius R2. The distal portion 40 extends from the central portion 38 and extends toward the longitudinal axis X in the second direction Y2. The distal portion 40 curves toward the longitudinal and has a radius R3.

In certain preferred embodiments of the invention, the outer member 12 has at least two different radii of curvature. In the embodiment shown, the central portion 38 has a radius R2 which is different from the radius R1 of the proximal portion. The outer member may have additional radii of curvature. For example, certain preferred embodiments have a distal portion 40 with a radius R3 which is different than the radius R2 of the central portion 38. Preferably, in the embodiment shown, R3 is less than R2. This causes distal portion 40 to curve or recurve back away from a vertical axis Y relative to longitudinal axis X. Preferably, distal portion 40 forms an angle a relative to vertical axis Y. This is best seen in FIG. 2. In addition, the distal portion 40 tends to close off the arcuate section 18 of the outer member 12, as R3 is less than R2.

While arcuate section 18 generally includes two different radii, arcuate section 18 may be provided with more than one different radii, for example R4, R5, etc., or a continuously varying radii. The shape of the outer member 12 enables the instrument to be disposed in the body in the intended manner, as discussed below.

Figure 3:
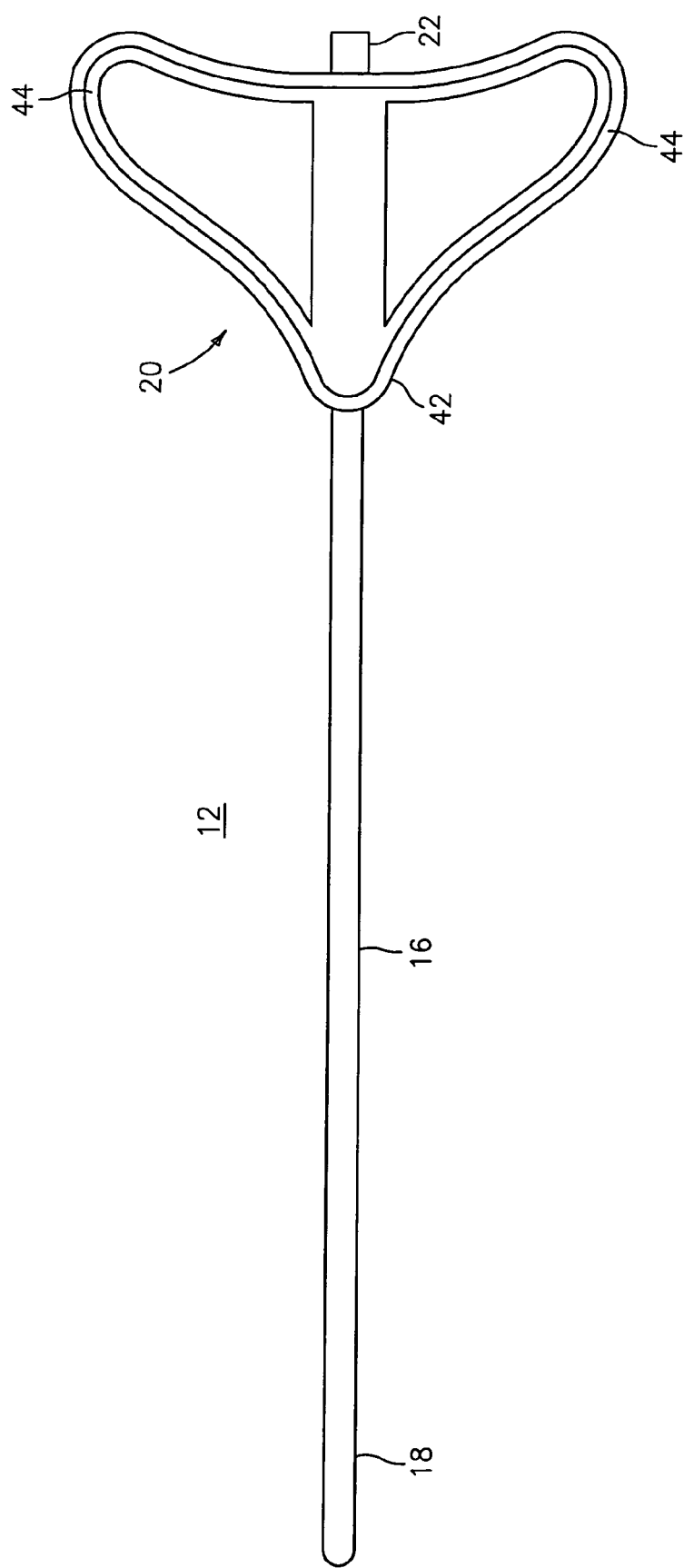
FIG. 3 is a bottom view of the outer member of the instrument in accordance with the embodiment of FIGS. 1 and 2.

Referring to FIG. 3, handle 20 desirably has a "delta wing" shape, or a shape with laterally extending portions. The handle 20 has a tapered front end 42 and wing-like lateral projections 44. This provides an ergonomic shape to facilitate comfortable and accurate manipulation of outer member 12. Preferably, handle 20 is formed of a plastic material and affixed adjacent proximal end 22 of outer member 12. The handle 20 is preferably oriented on the outer member 12 so as to be disposed in a plane generally perpendicular to the plane in which the arcuate section 18 is disposed. The orientation of the handle facilitates the manipulation of the instrument in the intended manner in the procedure.

Figure 4:
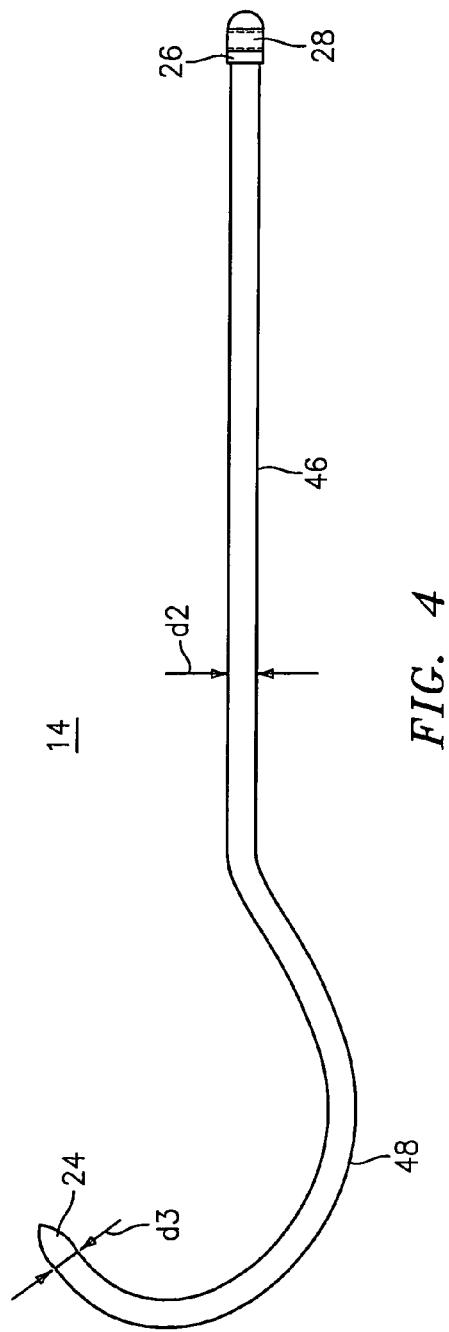
FIG. 4 is a side view of a stylet of the instrument in accordance with the embodiment of FIGS. 1–3.

The outer member 12 receives the stylet 14. Stylet 14 includes a conical tip 24 and a proximal end 26 having a hole or slot 28 for receipt of a length of material therethrough. As noted above, stylet 14 is provided to draw a length of material through the body. This can be done directly or through throughbore 30 of the outer member 12. Referring now to FIG. 4, stylet 14 is formed of a flexible material and generally has the shape of outer member 12, including a long section 46 and a curved section 48 extending distally from the long section 46. Stylet 14 is sufficiently flexible so as to pass through outer member 12 and has an outer diameter d2 which is smaller than the diameter of through bore 30, or the inner diameter of outer member 12. In order to allow the insertion of instrument 10 while avoiding the separation of stylet 14 from outer member 12, conical tip 24 has an outer diameter d3 which is greater than the diameter of the through bore 30.

Preferably, stylet 14 is formed of a color that is easily visible against tissue, such as, for example, blue, to assist in locating the stylet 14 during a surgical procedure. During such surgical procedure, instruments for visualizing the interior of the body may be used, such as, for example, equipment for performing a cystoscopy. The stylet 14 preferably has a color that facilitates visualization of the stylet 14 during a cystoscopy or using other techniques or equipment.

Figure 5:
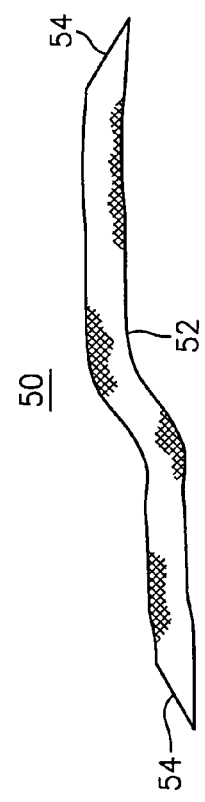
FIG. 5 is a perspective view of a length of material used with the instrument in accordance with the embodiment of FIGS. 1–4.
Figure 6:
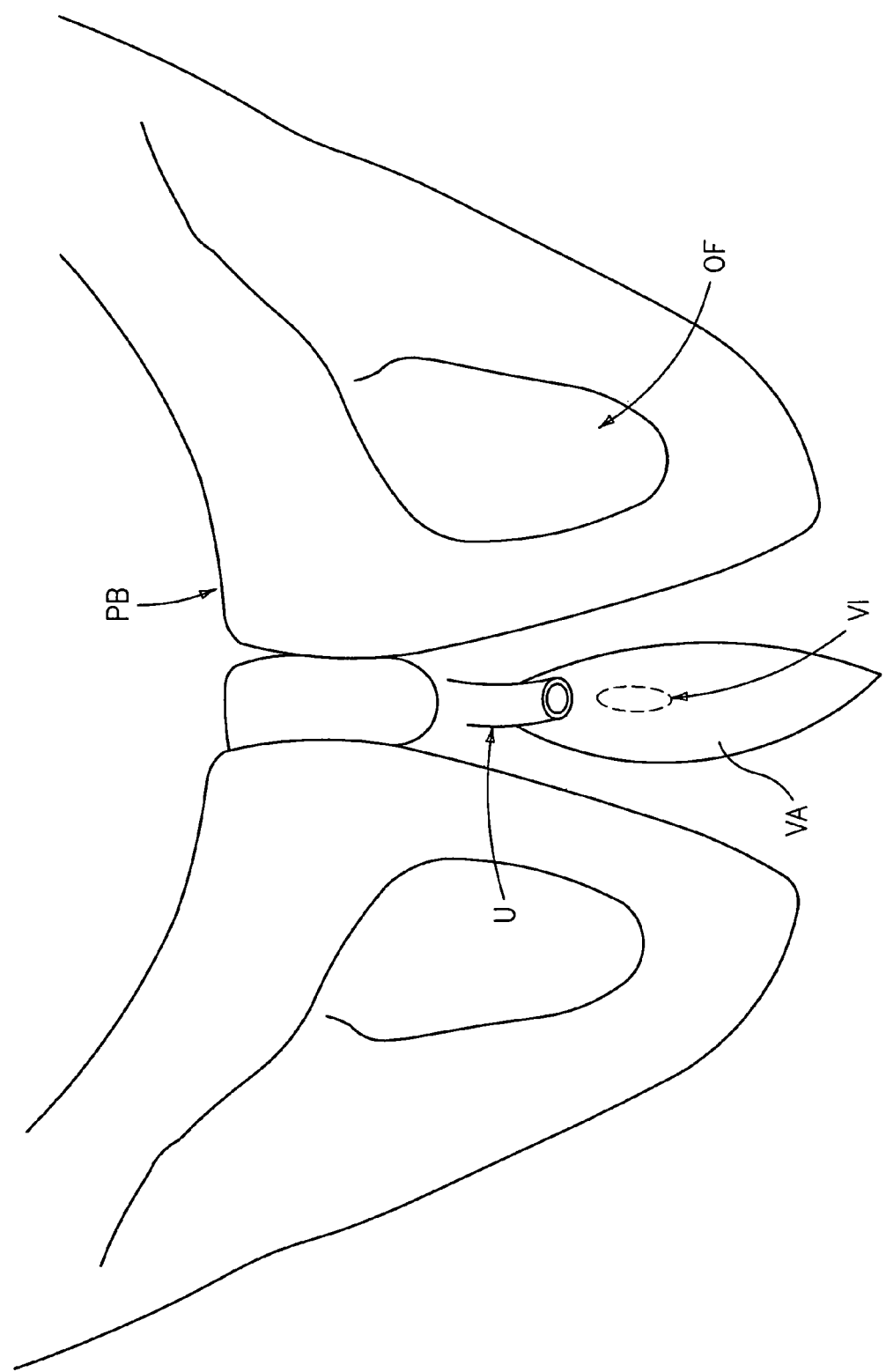
FIG. 6 is a sketch showing the relation of the vagina to the pelvis.

As noted above, instrument 10 is designed to facilitate insertion of a length of material into and through the body, such as, for example, in an intravaginal slingplasty procedure. Referring briefly to FIG. 5, a material such as a tape 50 can be used to support the urethra. Tape 50 has a generally uniform central portion 52 to support the urethra and tapered ends 54 to facilitate insertion of tape 50 through slot 28 in the proximal end 26 of stylet 14. Tapered ends 54 are preferably angle° relative to the central portion to facilitate insertion into slot 28 of stylet 14. The tape may be made from any mesh, including multifilament or monofilament mesh materials. The tape is preferably formed from the material disclosed in certain embodiments of U.S. Pat. No. 5,292,328, the disclosure of which is hereby incorporated by reference herein. Tape 50 is preferably formed from SurgiPro (trademark) polypropylene knitted tape available from United States Surgical, a division of Tyco Healthcare Inc. This material provides sufficient strength to support the urethra and allow anchoring of the ends of the tape subcutaneously as described in more detail hereinbelow. Alternatively, other materials may be used which have different types of knitted or woven structures, coatings or different bio-mechanical properties such as absorbable or semi-absorbable materials. Preferably, the tape comprises a multifilament mesh that is relatively pliable. Such materials are less abrasive to tissue than less pliable mesh or mesh comprising monofilament strands.

The use of the instrument to insert a length of tape for supporting the urethra will now be described. The procedure generally includes inserting the instrument through the obturator foramen of the pelvis to a midline vaginal incision. The stylet can then be used in order to pass the tape through the tissue. This is done first on one side and then repeated on the contralateral side. The tape is positioned beneath the midurethra to support the urethra to achieve continence. During insertion, the tape extends through the obturator foramen to a point beyond the skin incisions over the obturator foramen to allow adjustment by traction. After adjustment, the ends of the tape are sectioned subcutaneously and all the incisions are closed. Post operatively, fibrous tissue ingrowth occurs through the tape.

Referring to FIG. 3, there is illustrated a sketch of the vagina relative to the pubic bone. As shown, the obturator foramen (OF) exists both sides of the pelvis (PB) adjacent the vagina (VA) and the urethra (U).

Figure 7:
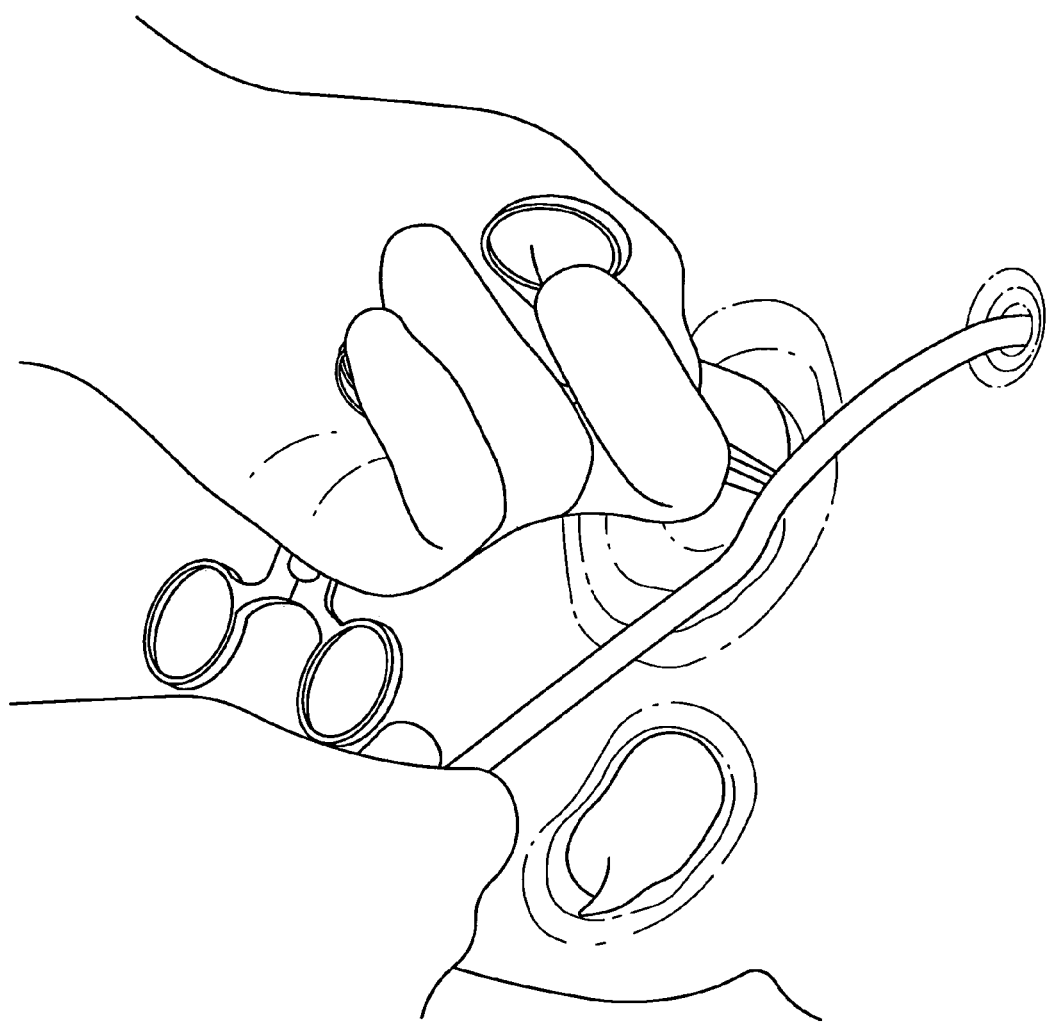
FIG. 7 is a black and white photograph of the vaginal area during an initial stage of a surgical procedure in accordance with a further embodiment of the invention.
Figure 8:
FIG. 8 is a black and white photograph similar to FIG. 7, during initial positioning of the instrument near the obturator foramen of the pelvis in the procedure in accordance with the embodiment of FIG. 7.

Referring now to FIGS. 7 and 8, a one to two centimeter mid-line incision is formed in the vaginal wall directly below the mid-point of the urethra. Using dissection scissors, the vaginal tissue is dissected laterally towards the obturator foramen on both sides to a depth of approximately two centimeters. The inferior internal rim of the obturator foramen is identified by digital examination. A small one centimeter skin incision is made at the most inferio-medial part of the obturator foramen. The size of the incisions made may vary and will depend upon the surgeon.

Figure 9:
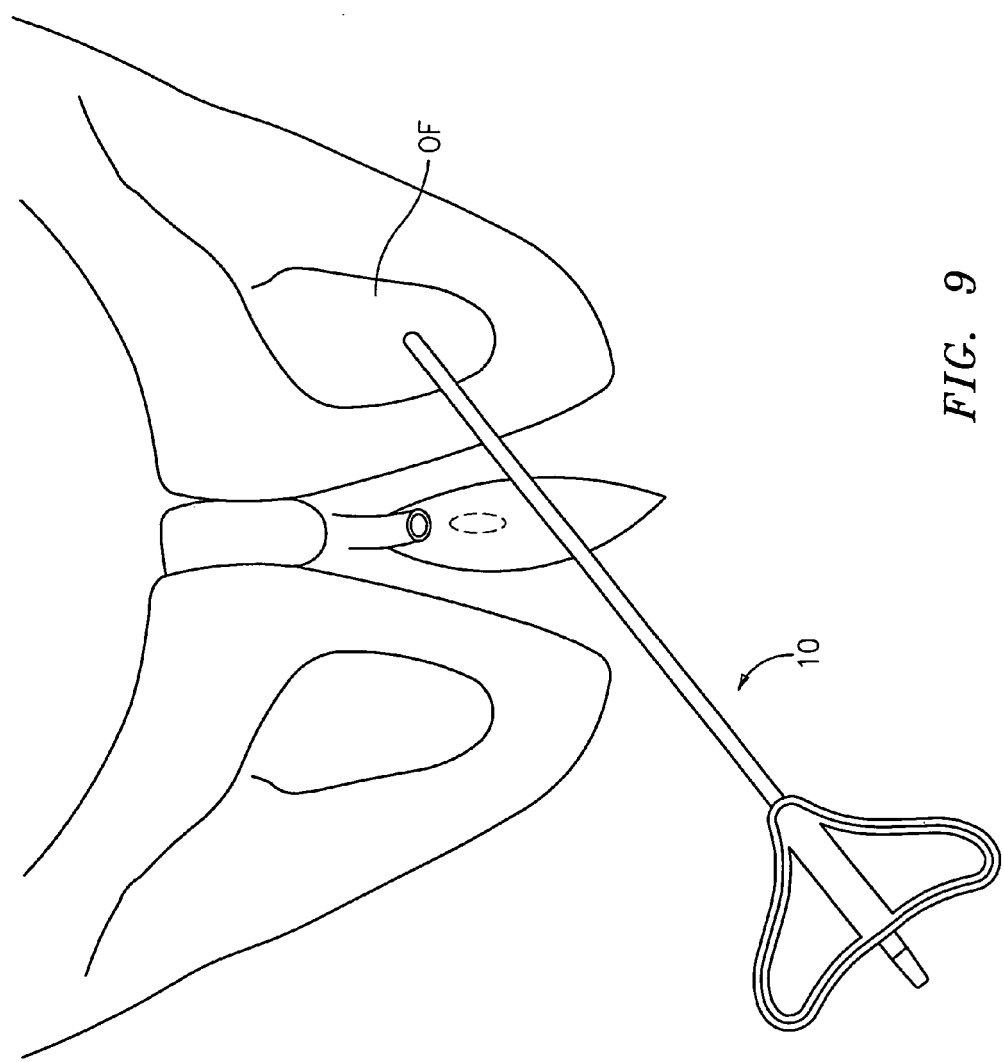
FIG. 9 is a sketch showing the instrument at the same stage as FIG. 8, in a procedure in accordance with the embodiment of FIGS. 7 and 8.

Referring to FIGS. 7–9, the instrument is held with the outer member 12 directed obliquely downwardly, at an approximately 45° angle, and toward the midline, with the handle 20 pointing obliquely towards the floor. The conical tip 24 is inserted into the incision over the obturator foramen. The conical tip 24 of the instrument is pressed carefully inwardly until the obturator membrane is pierced. During this movement, the angle of the instrument remains unchanged.

Figure 10:
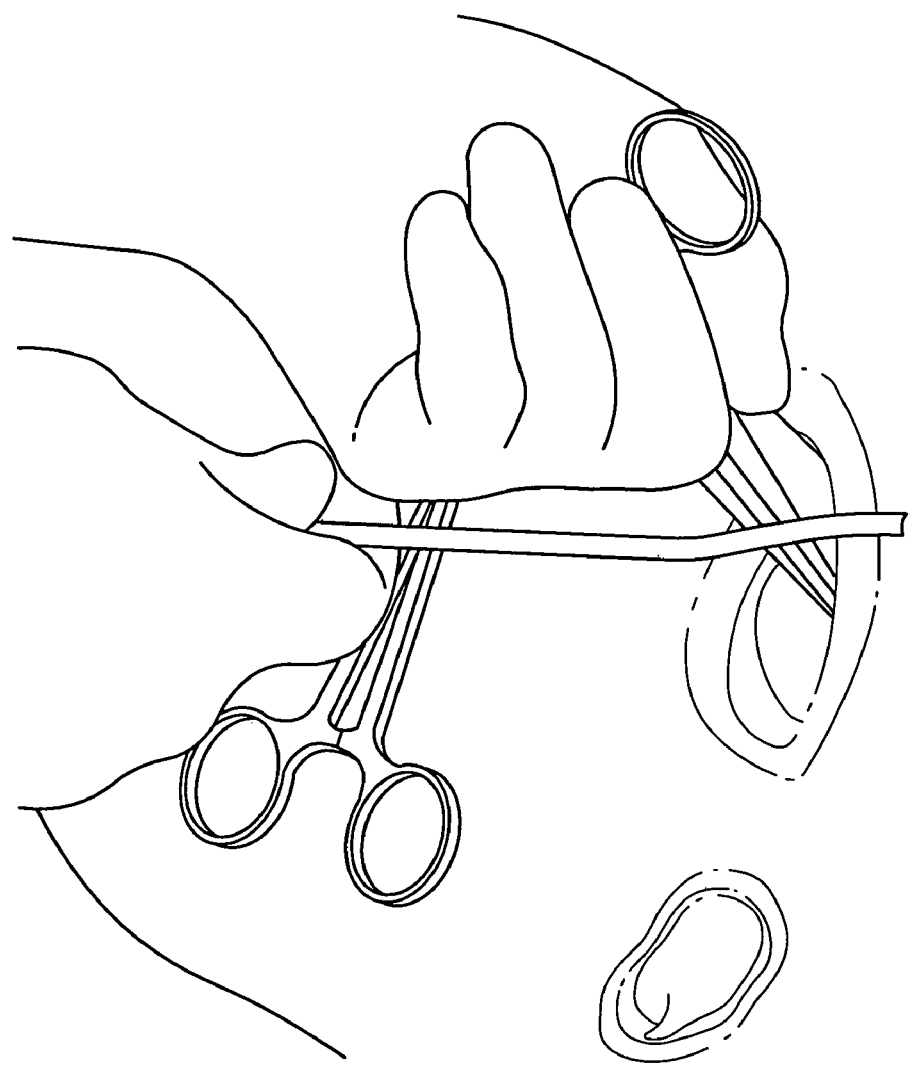
FIG. 10 is a black and white photograph showing the instrument turned about 45 degrees relative to the body, at a further stage in the procedure in accordance with the embodiment of FIGS. 7–9.
Figure 11:
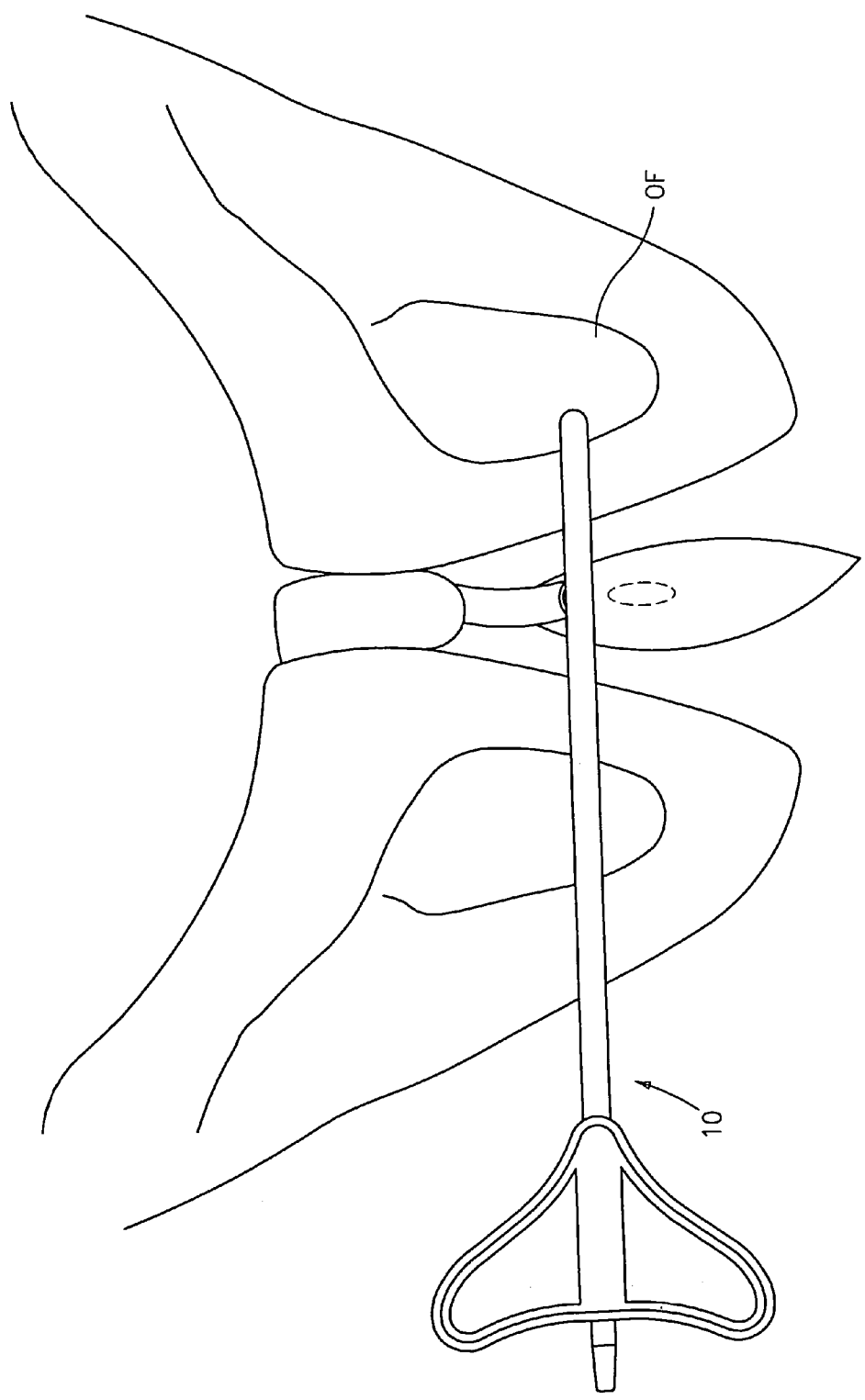
FIG. 11 is a sketch showing the instrument at the same stage as FIG. 10 in the procedure in accordance with the embodiment of FIGS. 7–10.
Figure 12:
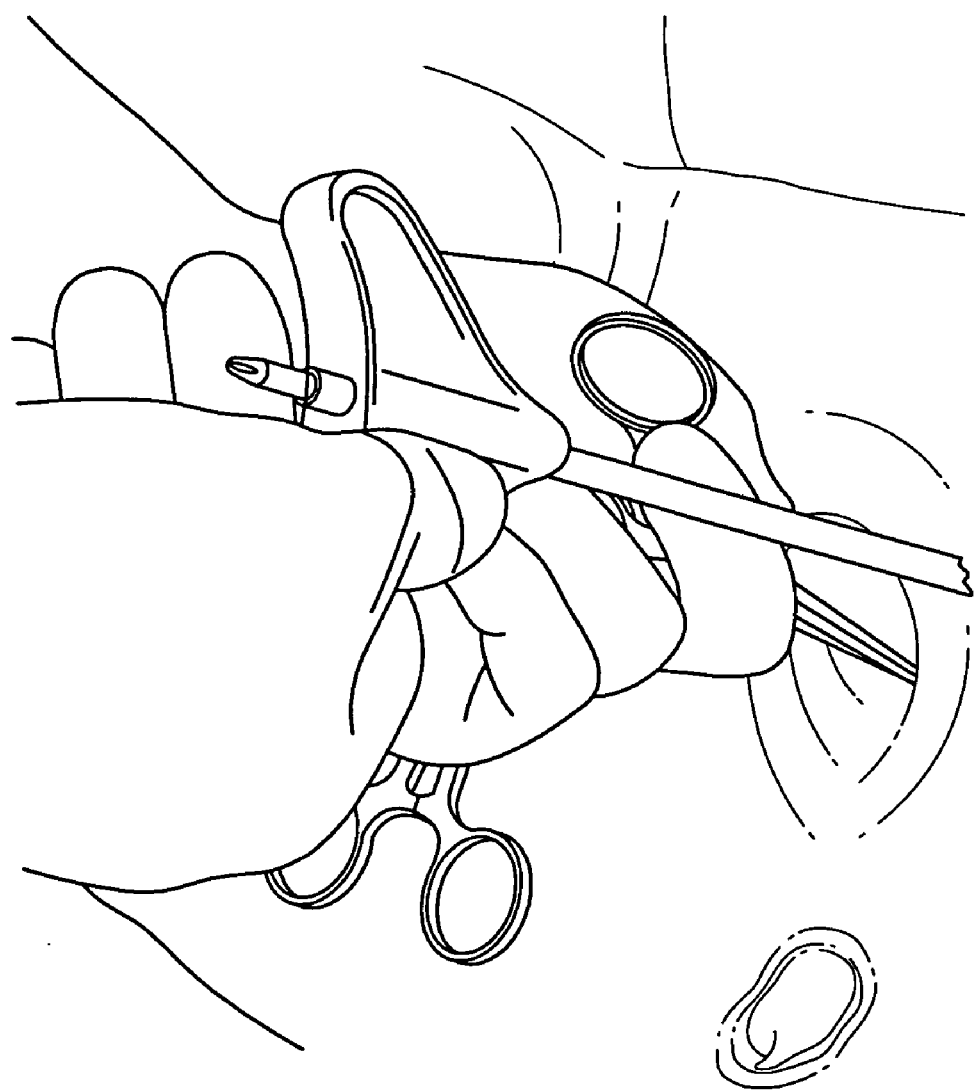
FIG. 12 is a black and white photograph showing the instrument rotated about ninety degrees to relative to the body, in a further stage of the procedure in accordance with the embodiment of FIGS. 7–11.

Referring to FIGS. 10 and 11, once the tip of the instrument has penetrated the obturator membrane, the instrument handle is turned towards a 90° angle relative to the body. Using one hand, the handle is then rotated away from the patient and toward the midline, allowing the tip of the instrument to pass through the obturator foramen, around the internal face of the bone and toward the vaginal incision (See FIG. 12).

Figure 13:
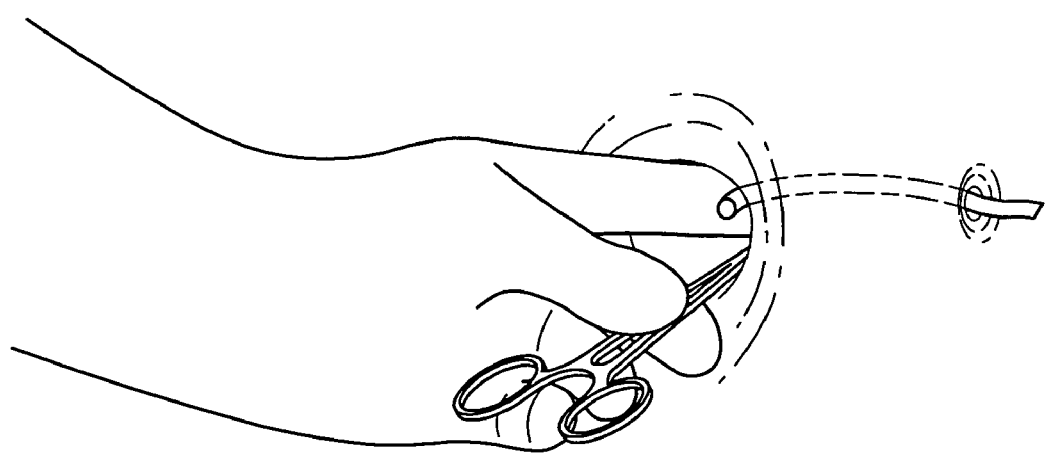
FIG. 13 is a black and white photograph showing the instrument rotated 180 degrees to pass through the obturator foramen and with the tip of the instrument exiting the vaginal incision at a further stage of the procedure in accordance with the embodiment of FIGS. 7–12.
Figure 14:
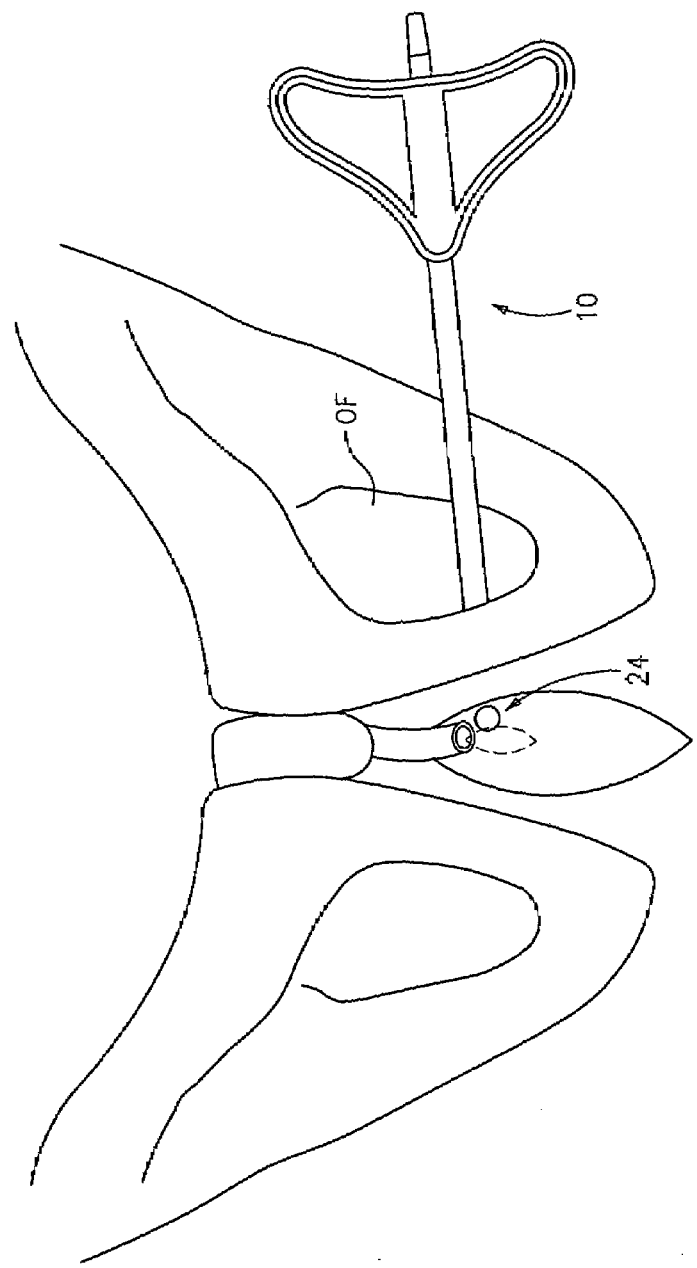
FIG. 14 is a sketch showing the instrument at the same stage as FIG. 13 in the procedure in accordance with the embodiment of FIGS. 7–13.

Referring to FIGS. 13 and 14, the exit of the tip of the instrument into the vaginal incision should be guided by a finger of the surgeon's free hand. The movement of the instrument is continued until the instrument handle has been rotated a full 180° and the tip of the instrument has exited the vaginal incision. As best seen in FIG. 13, the instrument extends from the incision over the obturator foramen to the vaginal incision.

Figure 15:
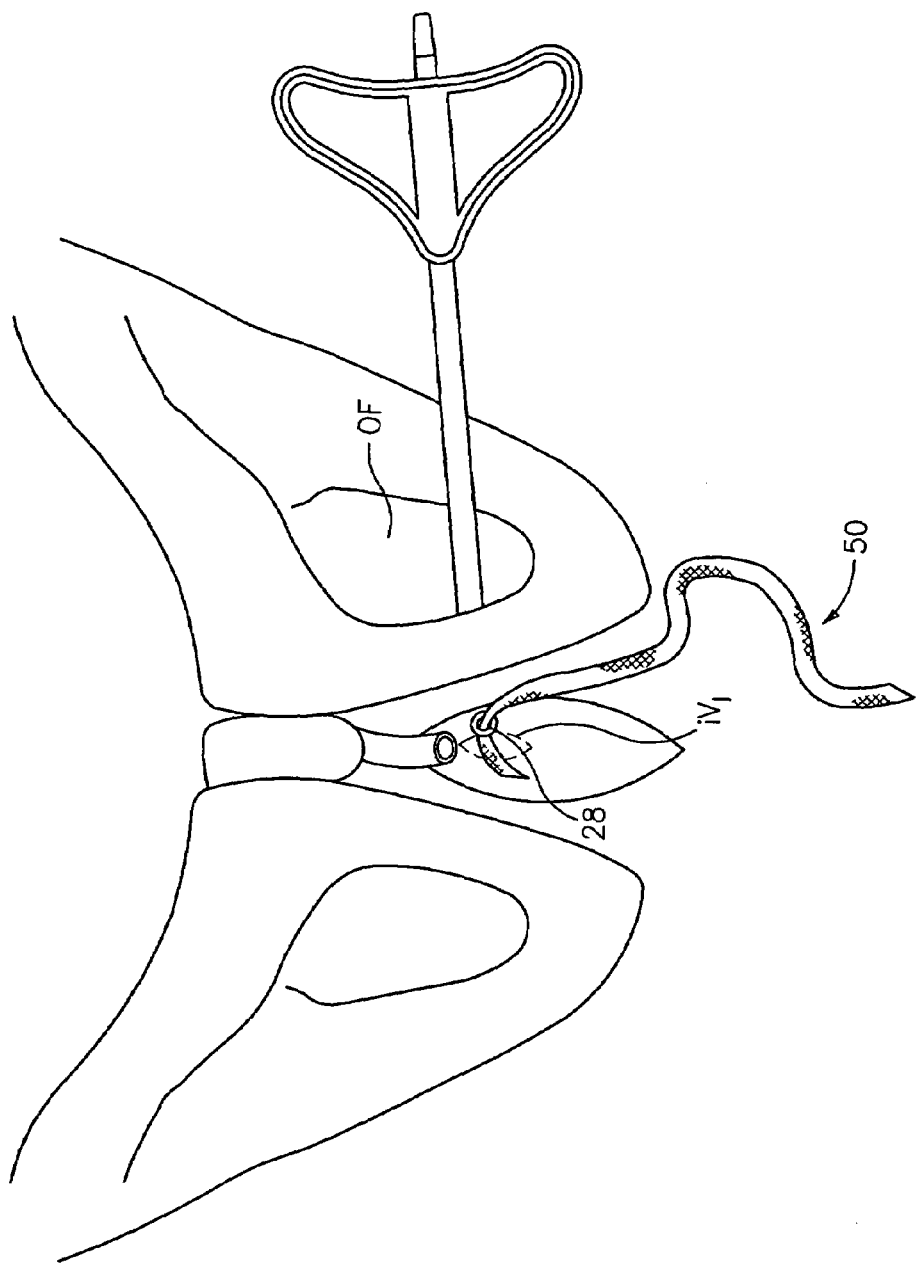
FIG. 15 is a sketch showing the tape threaded into the stylet at a further stage of the procedure in accordance with the embodiment of FIGS. 7–14.
Figure 16:
FIG. 16 is a black and white photograph showing the tape pulled through the vagina at a further stage of the procedure in accordance with the embodiment of FIGS. 7–15.
Figure 17:
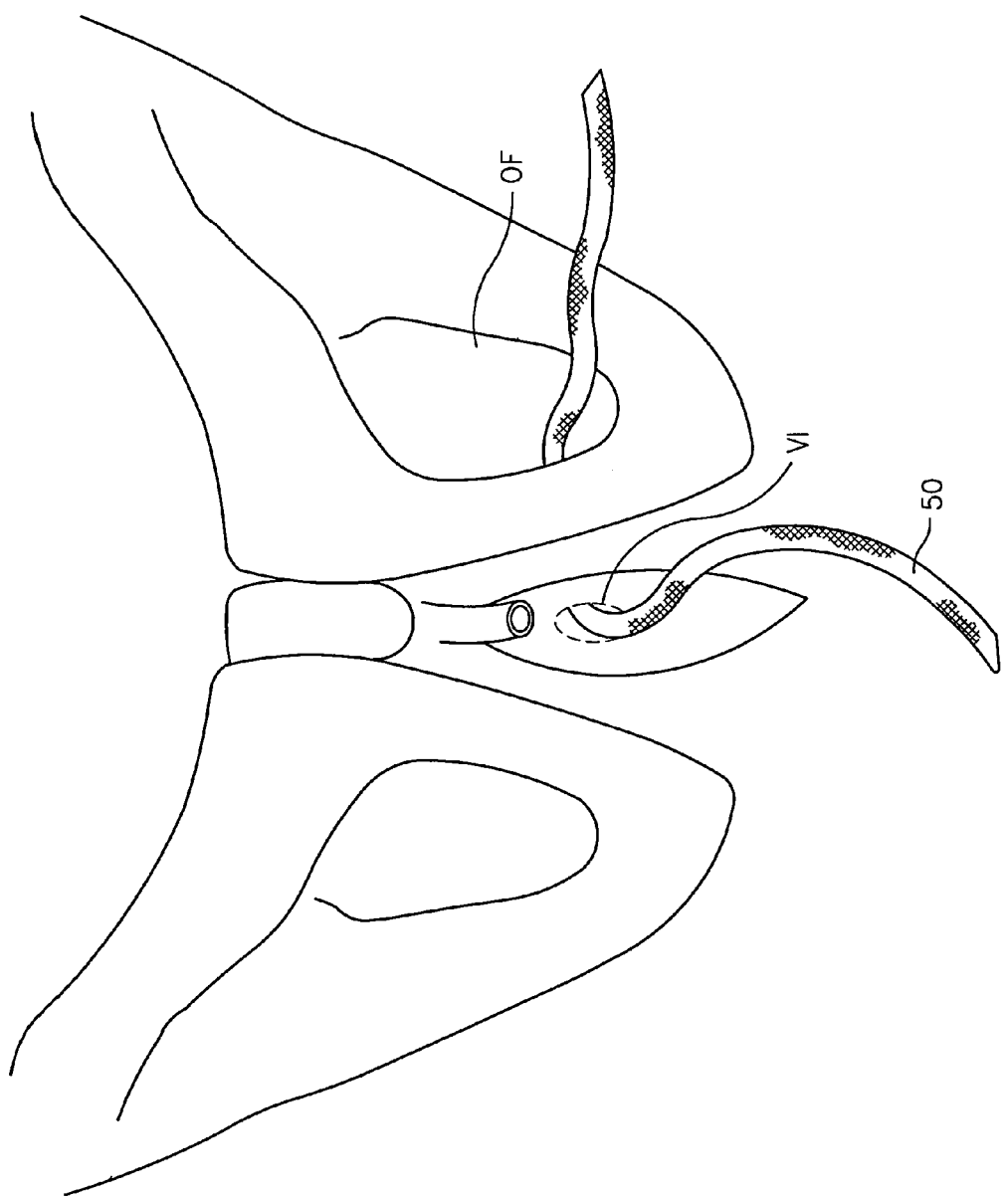
FIG. 17 is a sketch showing the tape extending from the incision through the obturator foramen and vaginal incision and out the vagina at the same stage as FIG. 16 in the procedure in accordance with the embodiment of FIGS. 7–16.

Referring to FIG. 15, the stylet 14 is then pulled through the outer member 12 and removed from the outer member 12. The stylet 14 is reinserted into the through bore of the outer member 12 in the reverse position so that the slot 28 is exposed at the vaginal extremity of the instrument. A tape 50 is then threaded into the slot 28 in the stylet 14 and the instrument is extracted to allow placement of the tape 50 between the vagina and the skin incision above the obturator foramen (FIG. 17).

Figure 18:
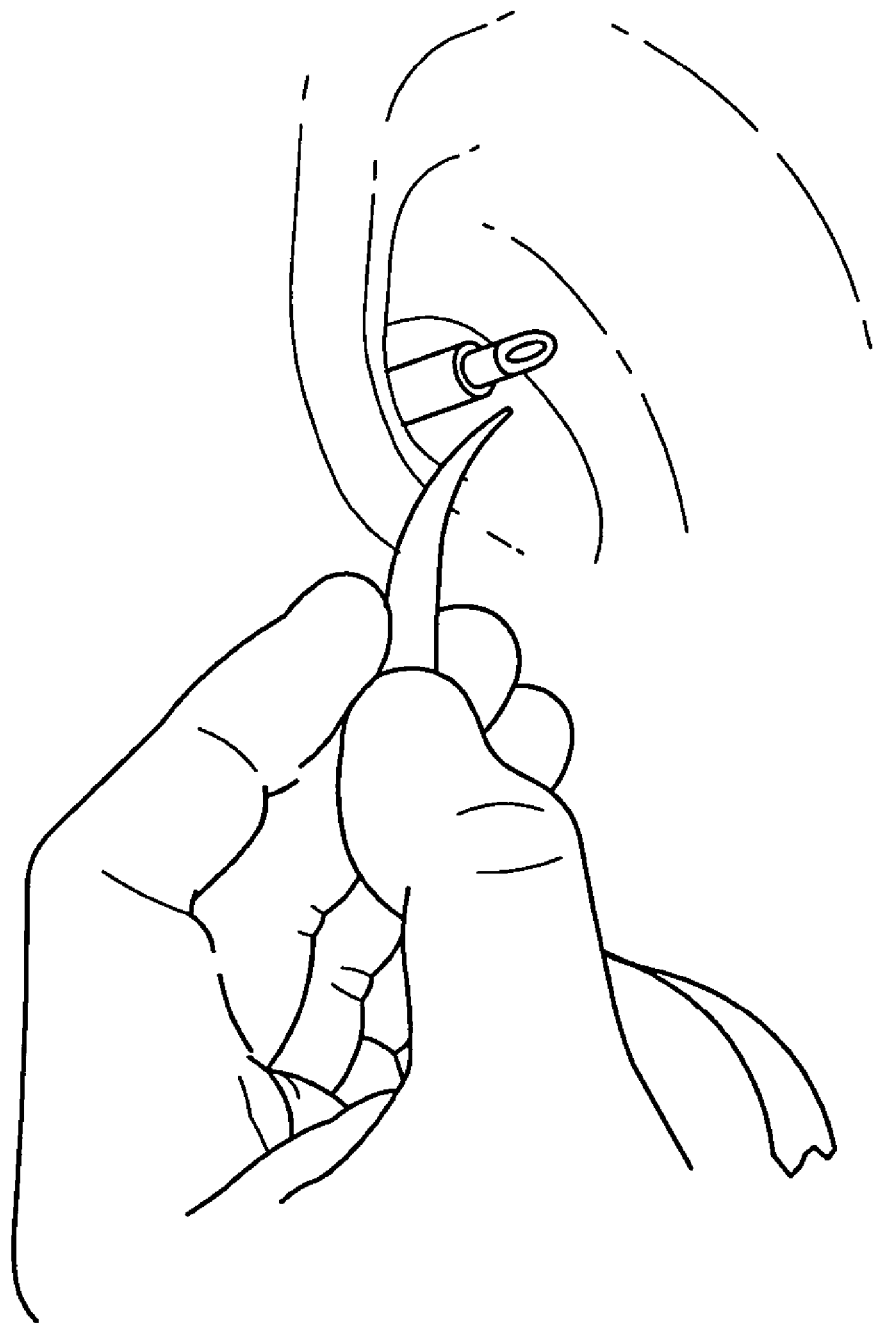
FIG. 18 is a black and white photograph showing the instrument in a position to receive a second end of the tape in a further stage of the procedure in accordance with the embodiment of FIGS. 7–17.
Figure 19:
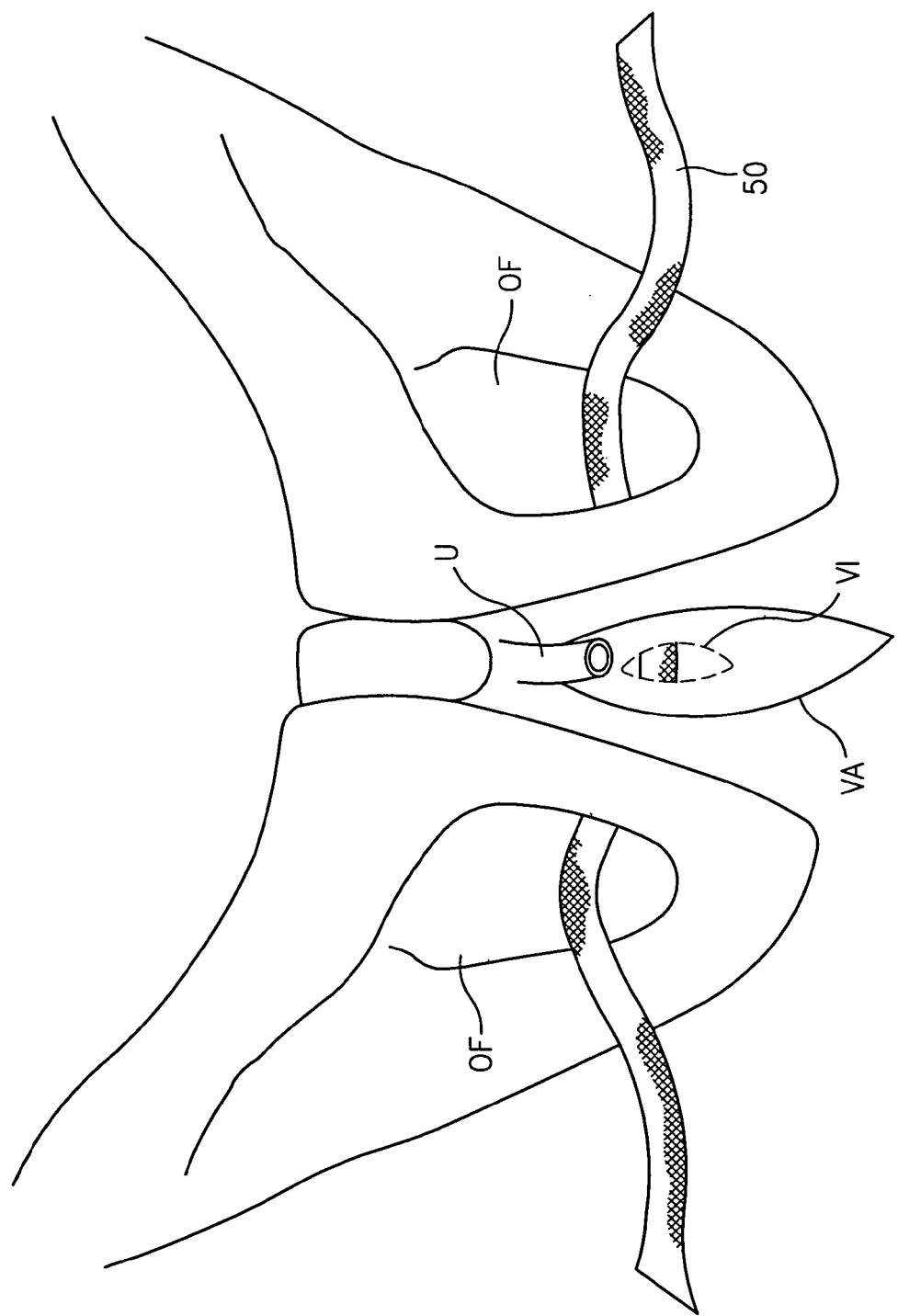
FIG. 19 is a sketch showing the tape passing through each obturator foramen on both sides of the pelvis and supporting the urethra in a further stage of the procedure in accordance with the embodiment of FIGS. 7–18.

Referring to FIGS. 18 and 19, the procedure is then repeated on the contralateral side in order to position the tape 50 beneath the mid-urethra, extending laterally towards the obturator foramen on both sides.

In a further embodiment of the invention, the stylet is not removed from the outer member 12 and reinserted so that the position of the stylet 14 is reversed. After the instrument has been passed through the obturator foramen on the first side, the tape may be inserted into the slot 28 in the stylet 14 exiting the proximal end of the outer member 12. The stylet 14 is drawn through the outer tubular member to draw the tape 50 out through the vaginal incision. Thereafter, the instrument may be removed, leaving the tape 50 extending from the incision over the obturator foramen, through the obturator foramen, and out the vaginal incision. The procedure on the obturator foramen on the second side is the same as discussed above.

It should be noted that during either procedure, the outer tubular member of the instrument shields the tape from engagement with the surrounding body tissues thereby preventing trauma to the tissue. Once the tape has been positioned beneath the midline of the urethra through each obturator foramen and out both incisions, the tape can then be adjusted by traction to be positioned flat beneath the urethra. The outer tubular member may be inserted into the urethra during the adjustment to act as a urethral splint. Once properly adjusted, the free ends of the tape are sectioned subcutaneously and the vaginal incision, as well as the incisions over each obturator foramen are closed to complete the procedure. The approach does not require the use of bone anchors, or additional anchoring structures. The patient's tissue holds the ends of the tape in place. Within about twenty-four hours, tissue ingrowth into the tape begins, which will further secure the tape.

In further embodiments of the invention, the procedure is carried out as discussed above in connection with FIGS. 7–19, except that after the instrument is positioned through the obturator foramen on the first side, the outer member 12 is removed, leaving the stylet 14 in place in the patient's body. The stylet 14 and tape 50 may be drawn through the body separately from the outer member 12.

In further embodiments of the invention, the procedure is carried out as discussed above in connection with FIGS. 7–19, except that after the instrument is positioned through the obturator foramen on the first side. The stylet is pulled through the outer member, drawing the tape from the vaginal incision to the incision over the obturator foramen.

Figure 20:
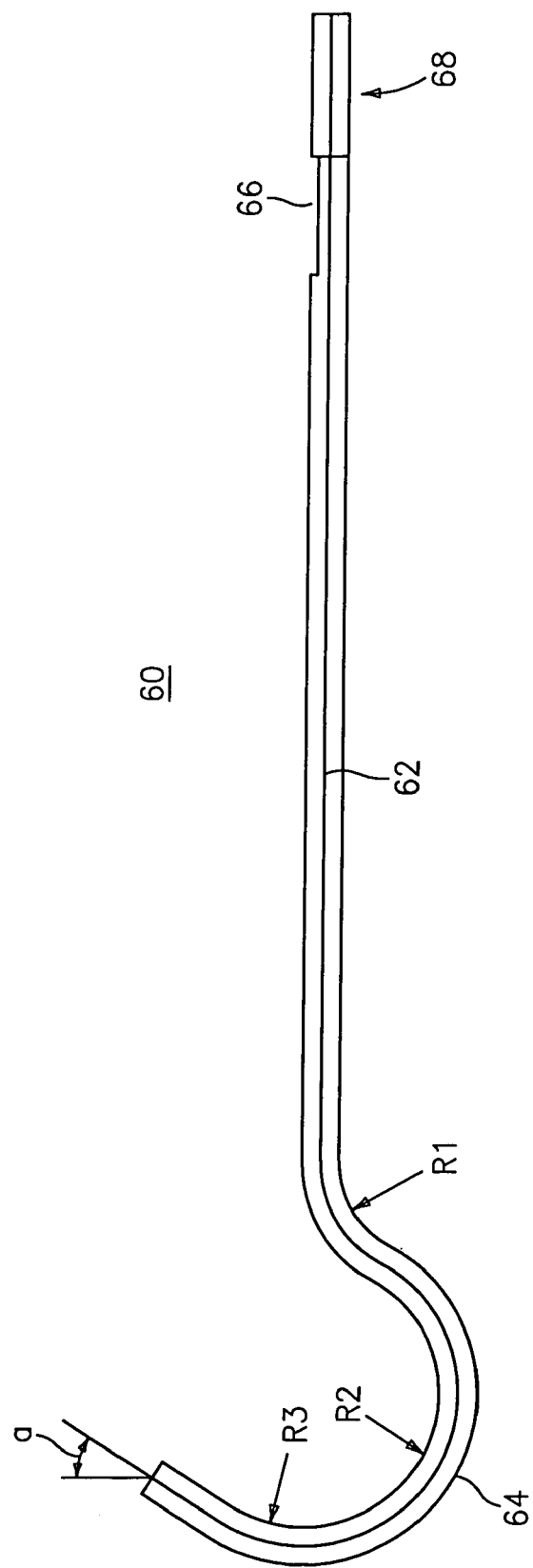
FIG. 20 is a side view of the outer tubular member of an instrument in accordance with a further embodiment of the invention.

Referring now to FIG. 20 there is illustrated an alternative embodiment of an outer tubular member configured to be used with a stylet such as, for example, stylet 14 described with respect to obturator instrument 10 above. Outer tubular member 60 generally includes a longitudinal section 62 defining a longitudinal axis X and an arcuate section 64 extending distally from longitudinal section 62 in a manner similar to that described hereinabove with respect to outer tubular member 12. Outer tubular member 60 desirably further includes a recess 66 formed adjacent a proximal end 68 of outer tubular member 60 to facilitate placement of a handle member.

In a preferred embodiment of outer tubular member 60, R1 is 17.5 units and R2 and R3 are 23 and 25 units respectively. Angle A is approximately 33°.

In the embodiment discussed above in connection with FIGS. 1–5, the inner stylet desirably comprises a blunt tip. The blunt tip is sufficient for bluntly tunneling through tissue and for penetrating the obturator membrane. In other embodiments, the tubular outer member, the inner stylet, or both, may have an incisive tip.

In the embodiment discussed above in connection with FIGS. 1–5, the stylet comprises a slot for receiving a length of tape. In other embodiments, the instrument is as discussed above in connection with FIGS. 1–5, except that the stylet comprises a feature for attaching the tape to the stylet, such as a snap-together part that engages a corresponding part on the tape. In other embodiments, the instrument is as discussed above in connection with FIGS. 1–5, except that the outer tubular member comprises a slot for receiving a length of tape. In further embodiments, the outer tubular member comprises a feature for attaching the tape to the stylet, such as a snap-together part that engages a corresponding part on the tape.

In further embodiments, the instrument is as discussed above in connection with FIGS. 1–5, except that the tape has an enlarged portion disposed between the ends of the tape. In further embodiments, the tape has other shapes, such as rectangular, circular, elliptical, arcuate, etc.

The instrument may comprise a tubular outer member and inner stylet, as discussed above, or a unitary introducer element. The tubular outer member and inner stylet has the advantage that the position of the stylet can be reversed with respect to the tubular member. In other words, the slot, or other feature for engaging the tape, may be positioned at the proximal end of the outer member or the distal end of the outer member. In addition, the tubular outer member shields the tape from the body, as the tape is pulled through the outer member. In embodiments employing a unitary introducer element, a sheath for enclosing the tape as the tape is passed through the body may be desired.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the invention as defined by the appended claims. For example, embodiments of the present invention encompass a unitary introducer element, as opposed to the outer tubular member and inner stylet discussed above. In certain embodiments, the surgical instrument for passing a material into a body in a minimally invasive procedure comprises an introducer element having a longitudinal section defining a longitudinal axis and an arcuate section extending distally from the longitudinal section, the arcuate section having at least two different radii of curvature. The material desirably comprises a tape of mesh material. The proximal end of the introducer element is desirably adapted to receive an end of the tape. In other embodiments, a distal end of the introducer element is desirably adapted to receive an end of the tape.

In certain embodiments, the surgical instrument for passing a material into a body in a minimally invasive procedure comprises an introducer element having a longitudinal section defining a longitudinal axis and an arcuate section extending distally from the longitudinal section, the arcuate section being dimensioned and curved whereby when in use and in position in the body, the arcuate section extends from the skin over the obturator foramen, through the obturator foramen, to the vaginal wall. The material desirably comprises a tape of mesh material. The proximal end of the introducer element is desirably adapted to receive an end of the tape. In other embodiments, a distal end of the introducer element is desirably adapted to receive an end of the tape.

In certain embodiments, the surgical instrument for passing a material into a body in a minimally invasive procedure comprises an introducer element having a longitudinal section defining a longitudinal axis and an arcuate section extending distally from the longitudinal section, the arcuate section having a proximal portion which curves away from the longitudinal axis in a first direction, the arcuate section having a distal portion which curves toward the longitudinal axis in a second direction. The material desirably comprises a tape of mesh material. The proximal end of the introducer element is desirably adapted to receive an end of the tape. In other embodiments, a distal end of the introducer element is desirably adapted to receive an end of the tape.

In a further aspect of the present invention, a surgical instrument for passing a material into a body in a minimally invasive procedure, comprises a first member having a longitudinal section defining a longitudinal axis and an arcuate section extending distally from the longitudinal section. The arcuate section is dimensioned and curved whereby when in use and in position in the body, the arcuate section extends from the skin over the obturator foramen, through the obturator foramen, to the vaginal wall. The shape of the first member facilitates the passing of the material into the body, in a minimally invasive procedure. The shape of the first member enables a material to be placed inside the body in a minimally invasive procedure so that the material extends through the obturator foramen.

In certain preferred embodiments, the first member comprises a hollow outer tubular member. A stylet is at least partially movable within the outer tubular member and engageable with a material to pass the material within the body. The hollow outer tubular member and stylet enable the surgeon to remove the stylet from the outer tubular member and reinsert the stylet in the opposite position with respect to the outer tubular member. This structure also facilitates the placement of the material so that the material extends from a first side of the pelvis to a second side of the pelvis.

Preferably, a proximal portion of the arcuate section curves away from the longitudinal axis in a first direction and defines a first radius of curvature. A distal portion of the arcuate section curves toward the longitudinal axis in a second direction and defines a second radius of curvature. A portion of the distal section desirably extends across the longitudinal axis in the second direction.

In certain embodiments, the distal portion of the arcuate section has a third radius of curvature, different from the second radius of curvature. The distal portion may have a central section and a distalmost section. The central section has the second radius and the distalmost section has the third radius. In certain embodiments, the second radius is larger than the third radius. In other embodiments, the second radius is smaller than the third radius.

The stylet is desirably flexible. In certain preferred embodiments, the stylet includes a slot at a first end for receipt of an end of a material. The stylet desirably includes a conical tip at a second end. A diameter of the conical tip may be greater than an inner diameter of the outer tubular member.

The outer tubular member desirably has a handle at a proximal end thereof. In certain preferred embodiments, the handle has a laterally extending portion. The arcuate section defines a first plane and the wing defines a second plane substantially perpendicular to the first plane.

The surgical instrument preferably includes a material and, in certain preferred embodiments, wherein the material comprises a generally flat tape. At least one end of the tape may be cut at an angle for ease of threading the tape into the stylet, in embodiments in which the stylet comprises a slot for receipt of the at least one end. The tape desirably comprises a material including multifilament strands, which may comprise polypropylene strands. The material may comprise a generally flat tape and the stylet may have a proximal end adapted to receive an end of the tape. The material may comprise an absorbable material.

The stylet is desirably positioned in the tubular member so that the proximal end of the stylet is located adjacent a proximal end of the tubular member. In certain preferred embodiments, the stylet has a distal end that is blunt. The distal end may comprise a blunt conical tip. In other embodiments, the stylet has a distal end that is sharp.

The arcuate portion has a proximal portion which curves away from the longitudinal axis in a first direction and a distal portion which curves toward the longitudinal axis in a second direction. The shape of the first member facilitates the passing of the material into the body, in a minimally invasive procedure. The shape of the first member enables a material to be placed inside the body in a minimally invasive procedure so that the material extends through the obturator foramen.

A stylet is at least partially movable within the outer tubular member and engageable with a material to pass the material within the body. The hollow outer tubular member and stylet enable the surgeon to remove the stylet from the outer tubular member and reinsert the stylet in the opposite position with respect to the outer tubular member. This structure also facilitates the placement of the material so that the material extends from a first side of the pelvis to a second side of the pelvis.

Preferably, a proximal portion of the arcuate section curves away from the longitudinal axis in a first direction and defines a first radius of curvature. A distal portion of the arcuate section curves toward the longitudinal axis in a second direction and defines a second radius of curvature. A portion of the distal section desirably extends across the longitudinal axis in the second direction. Desirably, the distal portion of the arcuate section has at least two different radii.

In certain embodiments, the distal portion of the arcuate section has a third radius of curvature, different from the second radius of curvature. The distal portion may have a central section and a distalmost section. The central section has the second radius and the distalmost section has the third radius. In certain embodiments, the second radius is larger than the third radius. In other embodiments, the second radius is smaller than the third radius.

The stylet is desirably flexible. In certain preferred embodiments, the stylet includes a slot at a first end for receipt of an end of a material. The stylet desirably includes a conical tip at a second end. A diameter of the conical tip may be greater than an inner diameter of the outer tubular member.

The outer tubular member desirably has a handle at a proximal end thereof. In certain preferred embodiments, the handle has a laterally extending portion. The arcuate section defines a first plane and the wing defines a second plane substantially perpendicular to the first plane.

The surgical instrument preferably includes a material and, in certain preferred embodiments, wherein the material comprises a generally flat tape. At least one end of the tape may be cut at an angle for ease of threading the tape into the stylet, in embodiments in which the stylet comprises a slot for receipt of the at least one end. The tape desirably comprises a material including multifilament strands, which may comprise polypropylene strands. The material may comprise a generally flat tape and the stylet may have a proximal end adapted to receive an end of the tape. The material may comprise an absorbable material.

The stylet is desirably positioned in the tubular member so that the proximal end of the stylet is located adjacent a proximal end of the tubular member. In certain preferred embodiments, the stylet has a distal end that is blunt. The distal end may comprise a blunt conical tip. In other embodiments, the stylet has a distal end that is sharp.

One method of suspending a portion of the urethra with a length of material comprises the steps of providing a surgical instrument having an outer tubular member including a longitudinal proximal end and a curved distal end and a stylet movable within the tubular member and configured to hold an end of the length of material. The method includes positioning the stylet within the tubular member. A vaginal incision and an incision located over the obturator foramen are made. The curved distal end of the surgical instrument is passed through the incision over the obturator foramen. The method includes manipulating the surgical instrument such that the curved distal end passes through the obturator foramen and out the vaginal incision. A proximal end of the stylet is engaged with a first end of the length of material, and the stylet is drawn through the tubular member to draw a portion of the length of material from the incision over the obturator foramen and through the vaginal incision.

The outer tubular member may be withdrawn through the incision over the obturator foramen leaving the length of material extending through the obturator foramen and out the vaginal incision. The step of passing the curved distal end of the surgical instrument through the incision over the obturator foramen desirably includes rotating the surgical instrument approximately 30 degrees upward in relation to the body. The surgical instrument is desirably elevated to position the curved distal end through the obturator foramen. The surgical instrument is rotated to pass the curved distal end through the obturator foramen and out the vaginal incision.

Another method of suspending a portion of the urethra comprises the steps of passing a curved distal end of a surgical instrument through the body so that the instrument extends between a vaginal incision and a skin incision located over the obturator foramen. The surgical instrument has an outer tubular member including a longitudinal proximal end and a curved distal end and a stylet movable within the outer tubular member. The stylet is drawn through the body to draw the length of material through the body, extending between the vaginal incision and the incision over the obturator foramen.

The step of passing the curved distal end of the instrument desirably includes inserting the curved distal end of the instrument into the incision over the obturator foramen and moving the curved distal end through the obturator foramen, out the vaginal incision. The step of passing the curved distal end of the instrument desirably includes inserting the curved distal end into the vaginal incision. During the step of passing the curved distal end of the instrument, the stylet is desirably disposed within the outer tubular member.

The method may include, after the step of passing, withdrawing the stylet from the outer tubular member. The stylet may be reinserted in the outer tubular member so that an end of the stylet adapted to receive the material is disposed at the vaginal incision. The material is desirably disposed so that the material is received by the end of the stylet.

The step of drawing may include withdrawing the stylet through the outer tubular member, thereby drawing the material through the outer tubular member, and removing the outer tubular member through the body. The step of drawing may include withdrawing the stylet and outer tubular member from the body, thereby drawing the material through the body.

The step of passing desirably comprises passing the instrument through the body on a first side of the pelvis and further desirably comprises passing the instrument through the body on a second side of the pelvis.

The material desirably comprises a tape having a first end and a second end and the step of drawing desirably includes drawing a first end of the tape through the body and drawing a second end of the tape through the body.

The invention claimed is:

1. A surgical instrument (10) for passing a material into a body in a minimally invasive procedure comprising:
   a first member (12) having a longitudinal section (16) defining a longitudinal axis and an arcuate section (18) extending distally from the longitudinal section, the first member comprising a hollow outer tubular member; and
   a stylet (14) at least partially movable within the outer tubular member and engageable with a material to pass the material within the body;
   wherein a proximal portion (36) of the arcuate section curves away from the longitudinal axis in a first direction and defines a first radius of curvature (R1),
   wherein a portion (38, 40) of the arcuate section distal of the proximal portion (36) curves toward the longitudinal axis in a second direction and defines a second radius of curvature (R2, R3).

2. The surgical instrument as recited in claim 1, wherein a distal portion (40) of the arcuate section has a third radius of curvature (R3), different from the second radius of curvature (R2).

3. The surgical instrument as recited in claim 2, wherein the portion of the arcuate section distal of the proximal portion (36) has a central section (38) and a distalmost section (40), the central section having the second radius (R2) and the distalmost section having the third radius (R3), the second radius (R2) being larger than the third radius (R3).

4. The surgical instrument as recited in claim 2, wherein the portion of the arcuate section distal of the proximal portion (36) has a central section (38) and a distalmost section (40), the central section having the second radius (R2) and the distalmost section having the third radius (R3), the second radius (R2) being smaller than the third radius (R3).

5. The surgical instrument as recited in claim 1, wherein a portion of the distal section extends across the longitudinal axis in the second direction.

6. The surgical instrument as recited in claim 1, wherein the stylet (14) is flexible.

7. The surgical instrument as recited in claim 1, wherein the stylet (14) includes a slot (28) at a first end (26) for receipt of an end of the material.

8. The surgical instrument as recited in claim 1, wherein the stylet (14) includes a conical tip (24) at a second end.

9. The surgical instrument as recited in claim 8, wherein a diameter (d3) of the conical tip (24) is greater than an inner diameter of the outer tubular member.

10. The surgical instrument as receipt in claim 1, wherein the outer tubular member (12) has a handle (20) at a proximal end (22) thereof.

11. The surgical instrument as recited in claim 10, wherein the handle has a laterally extending portion (44).

12. The surgical instrument as recited in claim 11, wherein the arcuate section (18) defines a first plane and the laterally extending portion defines a second plane substantially perpendicular to the first plane.

13. The surgical instrument as recited in claim 1, wherein the material comprises a generally flat tape (50).

14. The surgical instrument as recited in claim 13, wherein at least one end (54) of the tape (50) is cut at an angle for ease of threading the tape into the stylet.

15. The surgical instrument of claim 13, wherein the tape (50) includes multifilament strands.

16. The surgical instrument of claim 13, wherein the tape (50) includes polypropylene strands.

17. The surgical instrument of claim 1, wherein the material includes a generally flat tape (5) and the stylet (14) has a proximal end (26) adapted to receive an end (54) of the tape.

18. The surgical instrument of claim 17, wherein the stylet is positioned in the tubular member (12) so that the proximal end (26) of the stylet is located adjacent a proximal end (22) of the tubular member.

19. The surgical instrument of claim 1, wherein the stylet (14) has a distal end that is blunt.

20. The surgical instrument of claim 19, wherein the distal end comprises a blunt conical tip (24).

21. The surgical instrument of claim 1, wherein the stylet has a distal end that is sharp.

22. The surgical instrument of claim 13, wherein the tape includes an absorbable material.

* * * * *